United States Patent [19]

Bartish

[11] 4,171,461
[45] Oct. 16, 1979

[54] SYNTHESIS OF ETHANOL BY HOMOLOGATION OF METHANOL

[75] Inventor: Charles M. Bartish, Bethlehem, Pa.

[73] Assignee: Air Products and Chemicals, Inc., Allentown, Pa.

[21] Appl. No.: 939,082

[22] Filed: Sep. 1, 1978

[51] Int. Cl.² .............................................. C07C 29/00
[52] U.S. Cl. .................................... 568/902; 252/432; 423/286
[58] Field of Search ........................ 568/902; 423/286

[56] References Cited

U.S. PATENT DOCUMENTS

| | | | |
|---|---|---|---|
| 3,248,432 | 4/1966 | Riley et al. | 568/902 |
| 3,285,948 | 11/1966 | Butter | 568/902 |

OTHER PUBLICATIONS

Maybury et al., "J.C.S. Chem. Comm.", (1974), pp. 534–535.

Mitchell et al., "J.C.S. Chem. Comm.", (1976), pp. 172–173.

*Primary Examiner*—Joseph E. Evans
*Attorney, Agent, or Firm*—R. L. Brewer; E. Eugene Innis; Barry Moyerman

[57] ABSTRACT

This invention relates to an improvement in a process for producing ethanol by methanol homologation. The homologation is carried out by reacting methanol with hydrogen and carbon monoxide in a 1–2:1 mole ratio and a temperature of from about 175–230° C. and a pressure of 2,000–10,000 psig in the presence of a cobalt catalyst represented by formulas I and II.

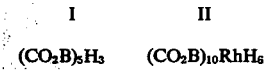

I  II $(CO_2B)_5H_3$  $(CO_2B)_{10}RhH_6$

6 Claims, No Drawings

SYNTHESIS OF ETHANOL BY HOMOLOGATION OF METHANOL

BACKGROUND OF THE INVENTION

1. Field of the Invention

This invention relates to an improved process for converting methanol to ethanol by reaction with hydrogen and carbon monoxide.

2. Description of the Prior Art

U.S. Pat. No. 1,562,480 appears to be the earliest work which discloses the preparation of valuable oxygenated compounds via the homologation of methanol. In the process, carbon monoxide, hydrogen and methanol are reacted in the presence of a catalyst to produce high molecular weight alcohols, such as isobutanol, normal propanol, amyl alcohol and others. The reaction is carried out in vapor phase and the catalyst used is one having hydrogenation and hydrating constituents. Often the catalyst is promoted with potassium oxide, chromium oxide and zinc oxide.

U.S. Pat. No. 2,623,906 discloses the preparation of oxygen-containing organic compounds by reacting methanol, carbon monoxide and hydrogen at pressures exceeding 1,000 atmospheres in the presence of a cobalt-containing catalyst, e.g., cobalt acetate, cobalt propionate, cobalt isobutyrate, etc.

U.S. Pat. No. 3,285,948 is representative of recent art (e.g., mid-60's) and discloses a process for producing ethanol by the catalytic interaction of methanol, carbon monoxide and hydrogen at a pressure of from about 1,000–15,000 psig and a temperature of about 175°–230° C. The interaction is carried out by utilizing a cobalt catalyst, an iodine promotor and a secondary promoter selected from the group consisting of ruthenium halides and osmium halides. Th patentee discloses the cobalt catalyst should be soluble in the reaction medium or form a cobalt carbonyl yielding compound. Examples of cobalt catalysts which can be converted to cobalt carbonyl forms include cobalt acetate, cobalt formate, cobalt propionate, etc.

U.S. Pat. No. 3,248,432 discloses an improved process for the synthesis of ethanol by reacting methanol, carbon monoxide and hydrogen in the presence of a water-soluble cobalt catalyst, iodine promoter and a phosphorous compound, e.g., diammonium phosphate.

U.S. Pat. No. 3,972,952 discloses a process for producing ethanol by the vapor phase reaction of methanol, hydrogen, and carbon monoxide in the presence of a solid catalyst, i.e., a support material impregnated with base promoters, e.g., oxides, hydroxides, or basic salts of an alalki or alkaline earth metal and metals of Periods 5 and 6 in Group 8 of the periodic table. Examples of inorganic base promoters include potassium or sodium oxide. The Period 5 and 6 metals of Group 8 include palladium, rhodium and platinum.

SUMMARY OF THE INVENTION

This invention relates to an improvement in a process for the liquid phase manufacture of ethanol by the homologation of methanol as represented by the equation $CH_3OH + CO + 2H_2 \rightarrow C_2H_5OH + H_2O$. The improvement resides in the use of a solid phase cobalt catalyst represented by formulas I and II.

$$\text{I} \qquad \text{II}$$
$$(CO_2B)_5H_3 \qquad (CO_2B)_{10}RhH_6$$

Significant advantages are obtained by utilizing the catalysts. These advantages include:

an ability to generate ethanol in good yield with substantial conversion of the methanol to ethanol and with little conversion to unwanted by-products;

a catalyst system which remains stable under reaction conditions and will not leach into the reactants as does the cobalt carbonyl catalysts of the prior art;

a catalyst system which is easy to separate from the reactants and products, i.e., it can be separated by simple filtration whereas the prior art soluble cobalt catalysts were separated by difficult extractive distillation.

DESCRIPTION OF THE PREFERRED EMBODIMENTS

I have found two cobalt catalysts to be particularly effective in catalyzing the homologation of methanol. They are solid at room temperature and pressure as well as at the reaction temperature and pressure of the homologation reaction. As a result, they can be easily removed from the reactants and products. The two catalysts are represented by formulas I and II with the second catalyst being a combination of cobalt and rhodium.

$$\text{I} \qquad \text{II}$$
$$(CO_2B)_5H_3 \qquad (CO_2B)_{10}RhH_6$$

The catalyst is utilized in the reaction mixture at a level to provide from about 0.01–0.5 moles cobalt, and preferably at a level to provide 0.04–0.07 moles cobalt per mole of methanol reactant. When the concentration of cobalt falls below about 0.05 moles, the yield of ethanol generally is substantially lower than when higher concentrations of catalysts are used.

The preferred catalyst is the formula II cobalt-rhodium catalyst. There seems to be some synergism between the cobalt and rhodium to produce a more efficient and effective catalyst as greater conversion to ethanol is noted. The broad and preferred concentration of catalyst based on cobalt, however, remains the same. However, the level of rhodium is only $5 \times 10^{-4}$ to 0.025 moles per mole of methanol.

Optionally, halide promoters can be used in combination with the cobalt hydride catalyst and these promoters include the ionic forms of iodine, e.g., potassium iodide, sodium iodide, lithium iodide as well as the molecular form of iodine. Other promoters commonly used include ruthenium halide or osmium halide with the concentration of metal being from about 0.003 to about 0.03 grams per mole of methanol. Surprisingly though, phosphorus promoter compounds, namely, trialkyl phosphine, have an extremely detrimental effect on the catalyst.

The additional reactants utilized in the process are carbon monoxide and hydrogen. The hydrogen and carbon monoxide are introduced into the reaction medium at a concentration from about 0.7–2.5 moles hydrogen per mole carbon monoxide. This range is conventional although it has been found that a ratio of about 0.9–1:1 results in fewer by-products and improves the yield of ethanol, even though the reaction stoichiometry calls for a 2:1 ratio.

The reaction time can vary, but the minimum amount of time is that sufficient to effect completion of the desired reaction. Ordinarily, the process is carried out in from a matter of a few hours to 20 hours with preferred reaction time being about 13 to 17 hours. Temperatures and pressures utilized are conventional, e.g., 175°–230° C. with a preferred range of from 190°–210° C. and the pressure is from 2000–10,000 psig with a preferred range from 4,000–6,000 psig.

There are particular advantages in using the catalysts of the present invention compared to those of the prior art. Because the catalysts disclosed herein are solid materials, even under reaction conditions, they may be used in fixed-bed reactors. Such a configuration allows for improved reactor design and processing advantages. Most importantly, the solid catalysts will allow easy separation of reactants and products from the catalyst. Such an improvement is dramatic compared to the prior art cobalt carbonyl catalysts, where pressure had to be let down, the catalyst had to be decomposed, the products had to be separated, and the catalyst had to be regenerated—all in all a very complex process.

In contrast to making a solid catalyst by adsorbing cobalt carbonyl onto a desirable support, the catalysts of this invention are themselves solids. More importantly, they remain solid under reaction conditions and will not dissolve in the reactants or products. Such behavior is markedly different from that of solids impregnated with cobalt carbonyl, because under reaction conditions the cobalt carbonyl will continually be backed from the support surface.

The following examples are provided to illustrate preferred embodiments of the invention and are not intended to restrict the scope thereof. All percentages are expressed as weight percentages.

EXAMPLE 1

Ethanol was synthesized in liquid phase in the following manner. First there was charged 128 grams (4 moles) of methanol and 15 grams (0.0232 moles) $(CO_2B)_5H_3$ to a 1-liter, glass-lined, 316 stainless steel, stirred autoclave. Then the autoclave was pressurized to 5,000 psia with a gaseous mixture of hydrogen and carbon monoxide (2:1 molar ratio $H_2$:CO). The reactants were heated to 180° C. under constant agitation for a period of 16 hours. After 16 hours, the reaction was terminated and the autoclave vented. The catalyst was removed from the reaction mixture by filtration. The filtrate product obtained was analyzed by gas chromotography and the analysis showed 2.8% methyl acetate, 83.6% methanol, 9.5% ethanol, 0.6% propanol and 3.5% water.

Assuming approximately 128 grams of product, the yield of ethanol was about 7% with conversion selectivity of methanol to ethanol being about 74%.

EXAMPLE 2

The procedure of Example 1 was repeated except that the temperature was maintained at 190° C. and the ratio of hydrogen to carbon monoxide was 1:1. The reaction product was analyzed and showed 8.9% methyl acetate, 57.2% methanol, 23.9% ethanol, and 9.9% water. On a basis of 128 grams of product, the ethanol conversion was about 16.6%, and conversion selectivity of methanol to ethanol was about 73%.

It is believed these results show that the 1:1 ratio of hydrogen to carbon monoxide and the increase in temperature improved the yield to ethanol as compared to Example 1.

EXAMPLE 3

The procedure of Example 2 was repeated except that 3.7 grams of $(CO_2B)_{10}RhH_6$ was utilized as the cobalt catalyst. The temperature remained at 190° C., and the hydrogen to carbon monoxide mole ratio was maintained at 1:1. At this level of catalyst, the molar ratio was 0.013 moles cobalt per mole methanol.

The reaction product was analyzed and found to contain 6.8% methyl acetate, 64% methanol, 13% ethanol, and 16.2% water. On a basis of 128 grams product produced, the yield calculated to be about 9.04% and the conversion selectivity to ethanol about 65.6%.

EXAMPLE 4

The procedure of Example 3 was repeated except that the catalyst concentration was increased from 3.7 grams to 16 grams. This calculates to provide about 0.053 moles cobalt per mole methanol in the reaction mixture.

The product was recovered and found to contain 11.1% methyl acetate, 44.6% methanol, 38% ethanol and 6.4% water. On a basis of 128 grams product produced, the yield was approximately 26% and the conversion selectivity was 78%. This particular example is significant to show that the increased catalyst concentration as compared to Example 3, results in a higher yield and slightly higher selectivity to ethanol.

EXAMPLE 5

The procedure of Example 2 was repeated except that 8 grams or 23 mmoles of prior art soluble catalyst of cobalt carbonyl, i.e., $Co_2(CO)_8$ was used in place of the solid phase cobalt catalyst. The reactor was maintained at 185° C. instead of 190°, and the pressure was maintained at 4,700 psi rather than 5,000 psi.

The product was recovered by conventional vacuum distillation after 16 hours, analyzed and found to contain 0.8% acetaldehyde, 13.1% methyl acetate, 36.8% methanol, 16% ethanol, 3.2% propanol, 1.1% butanol and 29% water. On a basis of 128 grams product produced, the results indicate an 11% yield of ethanol and a conversion selectivity to ethanol of approximately 46.7%.

This particular example shows that not only is the selectivity to ethanol much lower where the cobalt octacarbonyl catalyst is used, but there is the additional problem of separating the catalyst from the reaction product.

What is claimed is:

1. In an homologation process for the synthesis of ethanol wherein methanol is reacted in liquid phase with carbon monoxide and hydrogen in the presence of a cobalt catalyst, the improvement which comprises employing as said cobalt catalyst a solid phase cobalt compound represented by formulas I and II below:

I  II $(CO_2B)_xH_3$  $(CO_2B)_{10}RhH_4$

2. The process of claim 1 wherein the molar concentration of cobalt employed in said homologation reaction is from 0.01–0.5 moles per mole of methanol.

3. The process of claim 2 wherein the temperature for effecting reaction is from about 175–230° C.

4. The process of claim 3 wherein the pressure utilized for said reaction is from about 2,000–10,000 psig.

5. The process of claim 4 wherein the cobalt catalyst employed is that of formula II.

6. The process of claim 5 wherein said cobalt compound is present to provide from 0.04–0.07 moles cobalt per mole of methanol.

* * * * *